United States Patent
Dyballa et al.

(10) Patent No.: US 10,093,604 B2
(45) Date of Patent: Oct. 9, 2018

(54) HETEROCYCLIC SELENABISPHOSPHITES AND PROCESS FOR PREPARATION THEREOF

(71) Applicant: EVONIK DEGUSSA GMBH, Essen (DE)

(72) Inventors: Katrin Marie Dyballa, Recklinghausen (DE); Robert Franke, Marl (DE); Claudia Weilbeer, Bernburg (DE); Detlef Selent, Rostock (DE); Armin Börner, Rostock (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/370,454

(22) Filed: Dec. 6, 2016

(65) Prior Publication Data

US 2017/0158590 A1 Jun. 8, 2017

(30) Foreign Application Priority Data

Dec. 7, 2015 (EP) ..................................... 15198148

(51) Int. Cl.
*C07C 45/28* (2006.01)
*C07F 9/655* (2006.01)
*C07F 9/6574* (2006.01)

(52) U.S. Cl.
CPC .......... *C07C 45/28* (2013.01); *C07F 9/65522* (2013.01); *C07F 9/65527* (2013.01); *C07F 9/65742* (2013.01); *C07F 9/65744* (2013.01)

(58) Field of Classification Search
None
See application file for complete search history.

(56) References Cited

U.S. PATENT DOCUMENTS

| 2015/0336885 A1 | 11/2015 | Dyballa et al. |
| 2016/0010225 A1 | 1/2016 | Dyballa et al. |
| 2016/0010226 A1 | 1/2016 | Dyballa et al. |

FOREIGN PATENT DOCUMENTS

| DE | 102013203865 A1 | 9/2014 |
| DE | 102013203867 A1 | 9/2014 |
| EP | 2949646 A1 | 12/2015 |

OTHER PUBLICATIONS

Chemical Abstract Registry No. 859821-79-7, indexed in the Registry File on STN CAS Online Aug. 12, 2005.*
International Search Report for EP 15 19 8148 dated May 24, 2016. 1 page.
Selent, Detlef et al. Diastereoisomeric bisphosphite ligands in the hydroformylation of octenes: rhodium catalysis and HP-NMR investigations. Chemical Communications. 2008. 6203-6205.
Franke, R., Selent, D., and Börner, A. Applied Hydroformylation. American Chemical Society, ACS Publications, Chemical Reviews, 2012. 5675-5732.
Tricas, Hugo, et. al. Bulky monophosphite ligands for ethene hydroformylation, J. of Catalysis, 2012, 198-205.
Paine, Tapan Kanti, et. al. Manganese complexes of mixed O, X, O-donor ligands (X = S or Se): synthesis, characterization and catalytic reactivity, Dalton Trans. 2003, 3136-3144.
Kamer, Paul C. J. et. al. Phosphorus (III) Ligands in Homogeneous Catalysis: Design and Synthesis, John Wiley and Sons, LTD. 2012, 94-131.
Lin, He M., et. al. A novel and efficient synthesis of selenides. Arkivoc, 2012, 146-156.

* cited by examiner

*Primary Examiner* — Po-Chih Chen
(74) *Attorney, Agent, or Firm* — Smith, Gambrell & Russell, LLP

(57) ABSTRACT

Novel heterocyclic selenabisphosphites, process for preparation thereof and use thereof as ligand unit for preparing ligands for use in complexes.

16 Claims, No Drawings

HETEROCYCLIC SELENABISPHOSPHITES AND PROCESS FOR PREPARATION THEREOF

Novel heterocyclic selenabisphosphites, process for preparation thereof and use thereof as ligand unit for preparing ligands for use in complexes.

T. K. Paine describes a synthesis of 2,2'-selenobis(4,6-di-tert-butylphenol) using selenium dioxide. The preparation of 2,2'-selenobis(4,6-di-tert-butylphenol) is effected here in an acidic medium with addition of concentrated hydrochloric acid. The product is obtained with a yield of 25% (T. K. Paine et al., "Manganese complexes of mixed O, X, O-donor ligands (X=S or Se): synthesis, characterization and catalytic reactivity", Dalton Trans., 2003, 15, 3136-3144). It is particularly disadvantageous here that the yields are very low and therefore in need of improvement.

H. M. Lin et al., "A novel and efficient synthesis of selenides", ARKIVOC, 2012, viii, 146-156, discloses another multi-stage synthetic route using Grignard reagents. A synthetic route to selenobiaryl ethers is disclosed in which bromine must first be added onto the corresponding phenol in order to then react the product with magnesium to give a Grignard reagent. The Grignard reagent can then react with the added selenium before the actual coupling to give the biaryl ether:

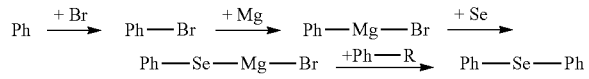

the product was obtained in a good yield, but this synthetic route is very complex, which makes it unattractive for industrial scale use. In this case, a multitude of synthetic steps are needed, the procedure for which is not uncritical in some cases, especially considering scale-up and using standards which are customary in industry. Moreover, this synthetic route gives rise to large amounts of waste products and solvents which have to be disposed of in a costly and inconvenient manner, one reason for which is the use of bromine.

EP 15168645.8 or U.S. Ser. No. 14/720,063 describes a large-scale economic synthetic route for preparing seleno-diphenols.

The reactions between olefin compounds, carbon monoxide and hydrogen in the presence of a catalyst to give the aldehydes comprising one additional carbon atom are known as hydroformylation or oxidation. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the status of hydroformylation of olefins is found in R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

Rhodium-monophosphite complexes in catalytically active compositions are suitable for the hydroformylation of branched olefins having internal double bonds. Since the 1970s, there have been descriptions of the use of "bulky phosphites" in hydroformylation (see, inter alia, van Leeuwen et al., Journal of Catalysis, 2013, 298, 198-205). These feature good activity, but the n/i selectivity for terminally oxidized compounds is low and in need of improvement.

In these hydroformylations, monophosphites and bisphosphites are generally used, which are often formed from biphenol units. The development of novel ligands is frequently limited by the available biphenol, that is, ligand units. For instance, 2,2'-selenobiaryl ethers and also diphenylselenoxides and diphenylselenides represent a highly interesting class of compound. The 2,2'-selenobiaryl ethers are currently only being used in certain complexes, especially those containing manganese, but they have great potential for further uses.

The object of the invention was to provide a further wholly novel substance class of ligands and ligand units in order to broaden the field of available ligands for the respective specific complexes in catalysis. The object also consisted of producing ligands for rhodium hydroformylation catalysts. The object therefore also consisted of novel intermediates as ligand units for preparing ligands. The objects are achieved with the heterocyclic selenaphosphites according to Claim 1, the process according to Claim 7 and the use according to Claim 15. Particular embodiments are disclosed in the dependent claims and also detailed in the description. The objects are preferably achieved by selenaphosphites of the structures I and Ia, especially with $R^1$ and/or $R^{1*}$ selected from structure II, IV, V, VI and VII. In the structures, the hydrogen-, alkyl- and/or —O—$(C_1-C_{12})$-alkyl-substituted compounds of $R^1$ and $R^{1*}$ in the structures mentioned are particularly preferred compounds.

The invention provides compounds of at least one heterocyclic selenaphosphite having a general structure I

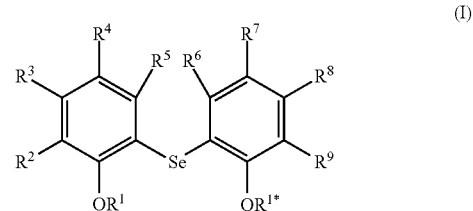

where $R^2$, $R^3$, $R^4$, $R^5$, $R^6$, $R^7$, $R^8$ and $R^9$ are each independently selected from: —H, —$(C_1-C_{12})$-alkyl, —O—$(C_1-C_{12})$-alkyl, —$(C_6-C_{20})$-aryl, —O—$(C_6-C_{20})$-aryl, -halogen, —OC═O—$(C_1-C_{12})$-alkyl, —S-alkyl, —S-aryl, —COO—$(C_1-C_{12})$-alkyl, —CONH—$(C_1-C_{12})$-alkyl, —CO—$(C_1-C_{12})$-alkyl, —CO—$(C_6-C_{20})$-aryl. —COOH, —SO$_3$H, —CN, —N[$(C_1-C_{12})$-alkyl]$_2$, where the alkyl and aryl groups may each independently be unsubstituted or substituted, especially comprising the alkyl and/or aryl groups in —$(C_1-C_{12})$-alkyl, —O—$(C_1-C_{12})$-alkyl, —$(C_6-C_{20})$-aryl, —O—$(C_6-C_{20})$-aryl, —OC═O—$(C_1-C_{12})$-alkyl, where the respective substituted —$(C_1-C_{12})$-alkyl group and substituted —$(C_8-C_{20})$-aryl group may have at least one substituent and the at least one substituent in each case may be selected independently from —$(C_3-C_{12})$-cycloalkyl, —$(C_3-C_{12})$-heterocycloalkyl, —$(C_6-C_{20})$-aryl, fluorine, chlorine, cyano, formyl, acyl or alkoxycarbonyl, and where the —$R^1$ and —$R^{1*}$ groups are independently selected from —H and at least one organofunctional phosphite group, synonymous with phosphorous esters, where at least one group of —$R^1$ and —$R^{1*}$ corresponds to an organofunctional phosphite group. The invention likewise provides compositions comprising at least one selenaphosphite of the structure I and mixtures of selenaphosphites of the structure I, for example the structures I, I and/or I shown below

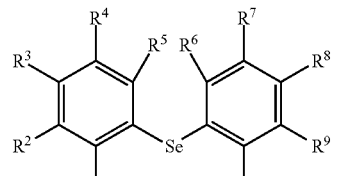
(I)

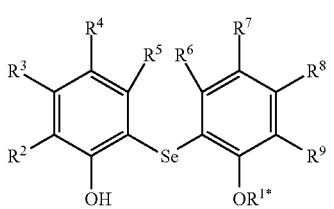
(I*)

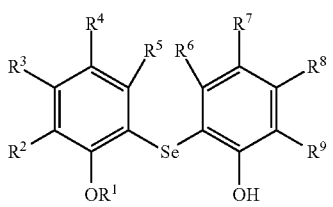
(I**)

with $R^2$, $R^3$, $R^4$, $R^5$, $R^6$, $R^7$, $R^8$ and $R^9$, $—R^1$ and $—R^{1*}$ corresponding to the definition defined above or below. The preparation of the compounds of the structures I* and I** may be of particular interest when the structures are to be used as a ligand unit.

The alkyl groups may in principle be linear, branched or cyclic. In a preferred alternative, the alkyl and aryl groups may each independently be unsubstituted.

In a preferred alternative, in the general structure I, the $—R^1$ and $—R^{1*}$ groups are independently selected from the structures II, III, IV, V, VI and VII.

According to a particularly preferred alternative, in the general structure I, the $—R^1$ and $—R^{1*}$ groups are the same and are selected from the structures II, III, IV, V, VI and VII. The invention further provides mixtures of the compound of the structure I in which $—R^1$ and $—R^{1*}$ are selected from —H and a structure of II, III, IV, V, VI and VII.

In a particularly preferred alternative, in the heterocyclic selenaphosphite of the general structure I,
 a) at least one group from $—R^1$ and/or $—R^{1*}$ corresponds to an organofunctional phosphite group and is selected from the structures II, III, IV, V, VI and VII

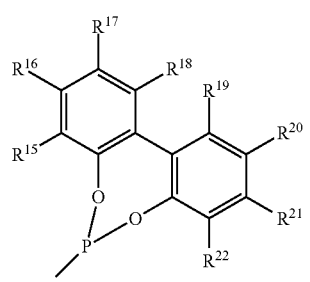
(II)

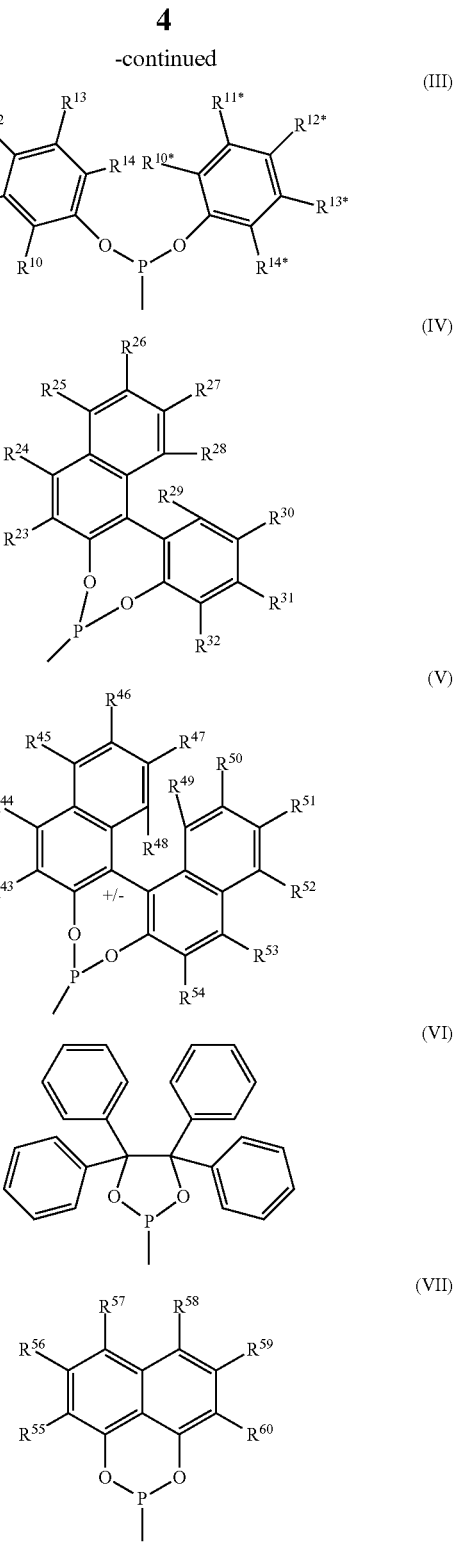

where the radicals
$R^{15}$, $R^{16}$, $R^{17}$, $R^{18}$, $R^{19}$, $R^{20}$, $R^{21}$, $R^{22}$ in structure II,
$R^{10}$, $R^{11}$, $R^{12}$, $R^{13}$, $R^{14}$, $R^{10*}$, $R^{11*}$, $R^{12*}$, $R^{13*}$, $R^{14*}$ in the structure III,
$R^{23}$, $R^{24}$, $R^{25}$, $R^{26}$, $R^{27}$, $R^{28}$, $R^{29}$, $R^{30}$, $R^{31}$ and $R^{32}$ in structure IV,
$R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure V, $R^{55}$, $R^{56}$, $R^{57}$, $R^{58}$, $R^{59}$ and $R^{60}$ in structure VII, in the respective structure are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, and/or b) —$R^1$ and —$R^{1*}$ are the same and may correspond to an organofunctional phosphite group and may be selected from the structures II, III, IV, V, VI and VII, or c) the selenaphosphite of the structure I takes the form of a mixture of a) and b).

Preferably, —$R^1$ and —$R^{1*}$ are the same and correspond to an organofunctional phosphite group and are selected from the structures II, IV, V, VI and VII.

The invention likewise provides heterocyclic selenaphosphites of the general structure I selected from at least one compound of the structure Ia

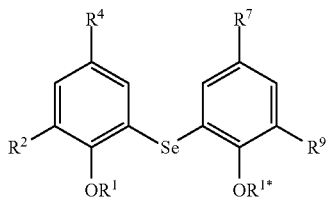

(Ia)

where $R^2$, $R^4$, $R^7$ and $R^9$ may each be independently selected from:

—($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, where —$R^1$ and —$R^{1*}$ in structure Ia are independently selected from —H and at least one organofunctional phosphite group, where at least —$R^1$ or —$R^{1*}$ corresponds to an organofunctional phosphite group. Preferably, —$R^1$ and —$R^{1*}$ are the same and correspond to an organofunctional phosphite group. In one alternative, —$R^1$ or —$R^{1*}$ is —H and the remaining —$R^1$ or —$R^{1*}$ corresponds to an organofunctional phosphite group. The latter compounds may, for example, also be used as a ligand unit. These compounds are suitable as a ligand unit since they contain an OH group that the person skilled in the art is able to convert further, by means of which ligands can be obtained.

In a further embodiment, the invention provides at least one heterocyclic selenaphosphite of the general structure I or Ia with —$R^1$ and —$R^{1*}$ selected from the structures II, III, IV, V, VI and VII as shown below:

where the $R^{15}$, $R^{16}$, $R^{17}$, $R^{18}$, $R^{19}$, $R^{20}$, $R^{21}$, $R^{22}$ radicals in structure II, $R^{10}$, $R^{11}$, $R^{12}$, $R^{13}$, $R^{14}$, $R^{10*}$, $R^{11*}$, $R^{12*}$, $R^{13*}$, $R^{14*}$ in the structure III, $R^{23}$, $R^{24}$, $R^{25}$, $R^{26}$, $R^{27}$, $R^{28}$, $R^{29}$, $R^{30}$, $R^{31}$ and $R^{32}$ in structure IV, $R^{43}$, $R^{44}$ $R^{45}$, $R^{46}$, $R^{47}$, $R^{48}$, $R^{49}$, $R^{50}$, $R^{51}$, $R^{52}$, $R^{53}$ and $R^{54}$ in structure V, $R^{55}$, $R^{56}$, $R^{57}$, $R^{58}$, $R^{59}$ and $R^{60}$ in structure VII, are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, the radicals especially being selected from —H, —($C_1$-$C_{12}$)-alkyl, —O—($C_1$-$C_{12}$)-alkyl, or from the alternatives a) —H and —($C_1$-$C_{12}$)-alkyl, b) —H and —O—($C_1$-$C_{12}$)-alkyl, or c) —H.

The invention likewise provides heterocyclic selenaphosphites of the general structure I selected from at least one compound of the structure Ia with —$R^1$ and —$R^{1*}$ selected from the structure II

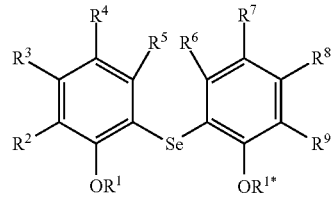

(I)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl or

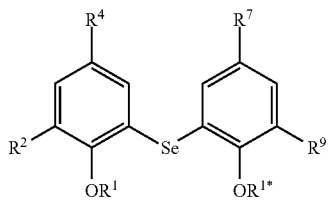

(Ia)

where $R^2$, $R^4$, $R^7$ and $R^9$ are each independently selected from:

—($C_1$-$C_{12}$)-alkyl, —O—($C_1$-$C_{12}$)-alkyl, and

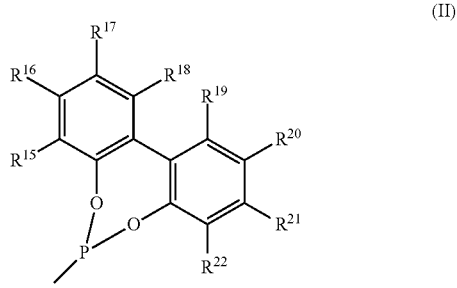

(II)

with $R^{15}$, $R^{16}$, $R^{17}$, $R^{18}$, $R^{19}$, $R^{20}$, $R^{21}$, $R^{22}$ in structure II each independently selected from: —H, —($C_1$-$C_{12}$)-alkyl, —O—($C_1$-$C_{12}$)-alkyl. Especially with $R^{15}$, $R^{16}$, $R^{17}$, $R^{18}$, $R^{19}$, $R^{20}$, $R^{21}$, $R^{22}$ in structure II selected from —H, —($C_1$-$C_{12}$)-alkyl; preferably, all $R^{15}$ to $R^{22}$ radicals are —H.

It may be preferable when —$R^1$ and —$R^{1*}$ in structure I or Ia are independently selected from —H and at least one organofunctional phosphite group, where at least one group from —$R^1$ and —$R^{1*}$ corresponds to an organofunctional phosphite group.

Further particularly preferred alternatives include heterocyclic selenaphosphites with —$R^1$ and —$R^{1*}$ selected from the alternatives a) —$R^1$ and —$R^{1*}$ in structure I or Ia are the same and are selected from II, III, IV, V, VI and VII, and/or b) in structure I or Ia, —$R^1$ is —H and —$R^{1*}$ is selected from II, III, IV, V, VI and VII, and/or c) in structure I or Ia, —$R^{1*}$ is —H and —$R^1$ is selected from II, III, IV, V, VI and VII, and/or d) the compound of alternative a) is in the form of a mixture with b) and/or c).

In structure Ia, $R^2$, $R^4$, $R^7$ and $R^9$ may each be independently selected from: -methyl, -ethyl, -tert-butyl, -isopentyl, -methoxy, -benzyl; -halogen.

In the structure II, $R^{15}$, $R^{16}$, $R^{17}$, $R^{18}$, $R^{19}$, $R^{20}$, $R^{21}$, $R^{22}$ may each independently be selected from: —H, -methyl, -ethyl, -tert-butyl, -isopentyl, -methoxy, -benzyl-; -halogen.

In the structure III, $R^{10}$, $R^{11}$, $R^{12}$, $R^{13}$, $R^{14}$, $R^{10*}$, $R^{11*}$, $R^{12*}$, $R^{13*}$, $R^{14*}$ may each independently be selected from: —H, -methyl, -ethyl, -tert-butyl, -isopentyl, -methoxy, -benzyl; -halogen.

In the structure VII, $R^{55}$, $R^{56}$, $R^{57}$, $R^{58}$, $R^{59}$ and $R^{60}$ may each independently be selected from: —H, -methyl, -ethyl, -tert-butyl, -isopentyl, -methoxy, -benzyl; -halogen.

The invention likewise provides a process for preparing at least one heterocyclic selenaphosphite of the general structure I and a heterocyclic selenaphosphite of the structure I obtainable by the process or a composition comprising mixtures of heterocyclic selenaphosphites of the structure I obtainable by the process

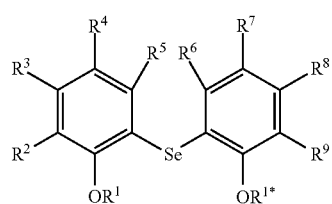

(I)

where $R^2$, $R^3$, $R^4$, $R^5$, $R^6$, $R^7$, $R^8$ and $R^9$ may each be independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —SO$_3$H, —CN, —N[($C_1$-$C_{12}$)-Alkyl]$_2$, where the alkyl and aryl groups may each be independently unsubstituted or substituted, wherein the respective substituted —($C_1$-$C_{12}$)-alkyl group and substituted —($C_6$-$C_{20}$)-aryl group may have at least one substituent and the at least one substituent in each case may be independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and
where the —$R^1$ and —$R^{1*}$ groups in structure I may independently be selected from —H and at least one organofunctional phosphite group, where at least one group of —$R^1$ and —$R^{1*}$ may correspond to an organofunctional phosphite group,
comprising at least the process step of
(i) reacting a selenodiaryl of the general structure IX

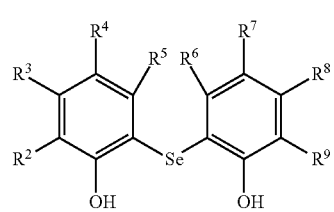

(IX)

where $R^2$, $R^3$, $R^4$, $R^5$, $R^6$, $R^7$, $R^8$ and $R^9$ may each be independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_2$)-alkyl, —CO—($C_6$-$C_{20}$)-aryl. —COOH, —SO$_3$H. —CN, —N[($C_1$-$C_{12}$)-Alkyl]$_2$, where the alkyl and aryl groups may each be independently unsubstituted or substituted, wherein the respective substituted —($C_1$-$C_{12}$)-alkyl group and substituted —($C_6$-$C_{20}$)-aryl group may have at least one substituent and the at least one substituent in each case may be independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, (ii) with at least one halophosphite compound $R^1$Hal of the formula Xa and/or $R^{1*}$Hal of the formula Xb, where Hal in each case is independently selected from fluorine, chlorine, bromine, iodine, preference being given to chlorine, where —$R^1$ and —$R^{1*}$ in formula Xa and/or Xb each independently correspond to an organofunctional phosphite group, —$R^1$ and —$R^{1*}$ preferably being the same, such that, preferably, $R^1$Hal of the formula Xa is the same as $R^1$Hal of the formula Xb, (ii) and obtaining at least one heterocyclic selenaphosphite of the general structure I or optionally a mixture of selenaphosphites of the structure I.

The hydroxy-functional heterocyclic selenaphosphites with $R^1$ or $R^{1*}$ being —H in the structures I*, I** I, Ia can preferably be obtained by an incomplete reaction of the selenadiaryl of the structure IX. In a preferred alternative, in the process, it is possible to use at least one halophosphite compound $R^1$Hal of the formula Xa and/or $R^{1*}$Hal of the formula Xb in which Hal is chlorine and a) —$R^1$ or —$R^{1*}$ may each independently be selected from the structures II, III, IV, V, VI and VII

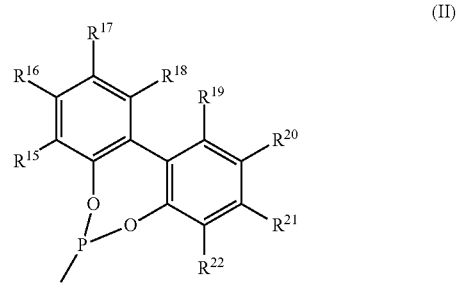

(II)

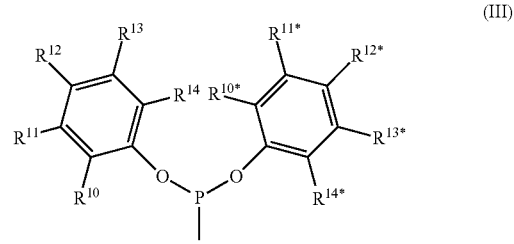

(III)

-continued

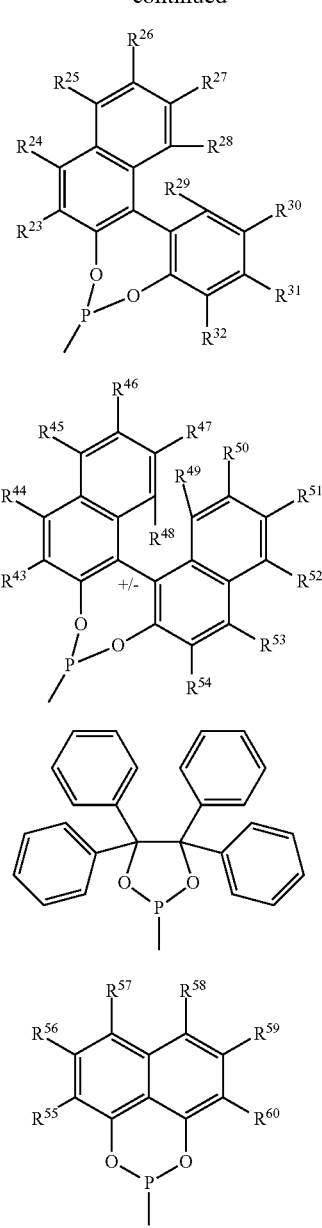

(IV)

(V)

(VI)

(VII)

where the radicals
$R^{15}$, $R^{16}$, $R^{17}$, $R^{18}$, $R^{19}$, $R^{20}$, $R^{21}$, $R^{22}$ in structure II, $R^{10}$, $R^{11}$, $R^{12}$, $R^{13}$, $R^{14}$, $R^{10*}$, $R^{11*}$, $R^{12*}$, $R^{13*}$, $R^{14*}$ in the structure III, $R^{23}$, $R^{24}$, $R^{25}$, $R^{26}$, $R^{27}$, $R^{28}$, $R^{29}$, $R^{30}$, $R^{31}$ and $R^{32}$ in structure IV, $R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure V, $R^{55}$, $R^{56}$, $R^{57}$, $R^{58}$, $R^{59}$ and $R_{60}$ in structure VII,
in the respective structure are each independently selected from: —H.
—$(C_1-C_{12})$-alkyl, —O—$(C_1-C_{12})$-alkyl, —$(C_6-C_{20})$-aryl, —O—$(C_6-C_{20})$-aryl, -halogen, and/or
b) —$R^1$ and —$R^{1*}$ may be the same and may be selected from the structures II, III, IV, V, VI, VI and VII.

The present invention likewise provides a process in which a halophosphite can be used, with the proviso that $R^1$Hal of the formula Xa and $R^{1*}$Hal of the formula Xb are the same, and Hal is chlorine and
—$R^1$ and —$R^{1*}$ are selected from the structures II, III, IV, V, VI and VII, where the $R^{15}$, $R^{16}$, $R^{17}$, $R^{18}$, $R^{19}$, $R^{20}$, $R^{21}$, $R^{22}$ radicals in structure II, $R^{10}$, $R^{11}$, $R^{12}$, $R^{13}$, $R^{14}$, $R^{10*}$, $R^{11*}$, $R^{12*}$, $R^{13*}$, $R^{14*}$ in the structure III, $R^{23}$, $R^{24}$, $R^{25}$, $R^{26}$, $R^{27}$, $R^{28}$, $R^{29}$, $R^{30}$, $R^{31}$ and $R^{32}$ in structure IV, $R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure V, $R^{55}$, $R^{56}$, $R^{57}$, $R^{58}$, $R^{59}$ and $R^{60}$ in structure VII, are each independently selected from: —H, —$(C_1-C_{12})$-alkyl, —O—$(C_1-C_{12})$-alkyl, —$(C_6-C_{20})$-aryl, —O—$(C_6-C_{20})$-aryl, -halogen.

In a further alternative, in the process, it is possible with preference to use a selenodiaryl of the general structure IXa

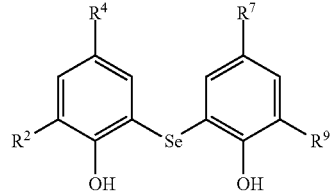

(IXa)

where $R^2$, $R^4$, $R^7$ and $R^9$ may each be independently selected from:
—$(C_1-C_{12})$-alkyl, —O—$(C_1-C_{12})$-alkyl, —$(C_6-C_{20})$-aryl, —O—$(C_6-C_{20})$-aryl, -halogen.

In a preferred process variant, (I) the reaction is effected in the presence of a base, especially an amine or a pyridine base, especially an alkylamine such as triethylamine or dimethylaminobutane, especially triethylamine.

For the reaction, the selenodiaryl of the general structure IX or IXa is reacted preferably with $R^1$Hal of the formula Xa and $R^1$Hal of the formula Xb, Xa and Xb preferably being the same, in a molar ratio of 10:1 to 1:10, preference being given to effecting the reaction in a molar ratio of 4:1 to 1:4, preferably of 2.5:1 to 1:2.5. It is further preferred when Hal is chlorine or bromine.

In addition, the (i) reaction is preferably conducted within the temperature range of −45 to 80° C., particularly of −15 to 30° C., especially of −5 to 25° C.

In addition, the (i) reaction is preferably conducted in an aprotic solvent; the solvent may especially be selected from organic aromatic halogenated solvents or hydrocarbons.

The invention likewise provides for the use of a heterocyclic selenaphosphite as ligand in a complex comprising at least one metal atom, especially when —$R^1$ and —$R^{1*}$ correspond to an organofunctional phosphite group; more preferably, the compound of the structure I or Ia can be used for catalysis of a hydroformylation reaction. Alternatively, it is possible to use a heterocyclic selenaphosphite in which —$R^{1*}$ or —$R^1$ is —H and the remaining group corresponds to an organofunctional phosphite group as an intermediate for preparation of ligands.

The invention likewise provides a complex comprising
at least one compound of the general structure (I) or (Ia) and
at least one metal atom selected from Rh, Ru, Co, Ir.

The invention further provides a process comprising the steps of
(i) initially charging at least one olefin,
(ii) adding a complex comprising
at least one compound of the general structure (I) or (Ia) and
at least one metal atom selected from Rh, Ru, Co, Ir, or a compound of the general structure (I) or (Ia) and a substance having a metal atom selected from Rh, Ru, Co, Ir, preferably Rh, Ir, Ru, more preferably Rh, (iii) feeding in $H_2$ and CO,
(iv) heating the reaction mixture,
wherein the olefin is converted to an aldehyde.

Process steps (i), (ii), (iii) and (iv) can be conducted in any desired sequence.

The terms "phenol", "aryl" and "phosphite" are used as generic terms in this application and therefore also encompass substituted structures of the compounds mentioned.

The aforementioned definition of substituted —$(C_1$-$C_{12})$-alkyl groups and substituted —$(C_6$-$C_{20})$-aryl groups apply to all groups in which these alkyl or aryl groups are present, i.e. especially also to the following groups: —O—$(C_1$-$C_{12})$-alkyl, —$(C_6$-$C_{20})$-aryl, —O—$(C_6$-$C_{20})$-aryl, —OC=O—$(C_1$-$C_{12})$-alkyl.

One or more substituents in the aforementioned structures of the selenophosphites and selenodiaryls comprise preferably 1 to 10 substituents, in particular 1 to 3.

In the context of the invention, the expression "—$(C_1$-$C_{12})_2$-alkyl" encompasses straight-chain and branched alkyl groups. Preferably, these groups are unsubstituted straight-chain or branched —$(C_1$-$C_8)$-alkyl groups and most preferably —$(C_1$-$C_6)$-alkyl groups. Examples of —$(C_1$-$C_{12})$-alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl,
2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl,
1,3-dimethylbutyl, 2,3-dimethylbutyl, 3,3-dimethylbutyl, 1,1,2-trimethylpropyl,
1,2,2-trimethylpropyl, 1-ethylbutyl, 1-ethyl-2-methylpropyl, n-heptyl, 2-heptyl,
3-heptyl, 2-ethylpentyl, 1-propylbutyl, n-octyl, 2-ethylhexyl, 2-propylheptyl, nonyl, decyl.

Halogen as substituent on alkyl or aryl includes fluorine, chlorine, bromine and iodine, particular preference being given to chlorine and fluorine.

All elucidations relating to the expression —$(C_1$-$C_{12})$-alkyl in the aforementioned structures of the selenaphosphites and selenodiaryls according to the invention also apply to the alkyl groups in —O—$(C_1$-$C_{12})$-alkyl, that is, in —$(C_1$-$C_{12})$-alkoxy.

Preference is given to unsubstituted straight-chain or branched —$(C_1$-$C_6)$-alkoxy groups.

Substituted —$(C_1$-$C_{12})$-alkyl groups and substituted —$(C_1$-$C_{12})$-alkoxy groups in the aforementioned structures of the selenaphosphites and selenodiaryls may have one or more substituents, depending on their chain length. The substituents are preferably each independently selected from: —$(C_3$-$C_{12})$-cycloalkyl, —$(C_3$-$C_{12})$-heterocycloalkyl, —$(C_6$-$C_{20})$-aryl, fluorine, chlorine, cyano, formyl, acyl or alkoxycarbonyl. This definition applies to all substituted alkyl or alkoxy groups of the present invention.

All elucidations relating to the expression —$(C_6$-$C_{20})$-aryl in the aforementioned structures of the selenaphosphites and selenodiaryls according to the invention also apply to the aryl groups in —O—$(C_6$-$C_{20})$-aryl.

Preference is given to unsubstituted —O—$(C_6$-$C_{20})$— groups.

In the context of the present invention, the expression "—$(C_6$-$C_{20})$-aryl and —$(C_6$-$C_{20})$-aryl-$(C_6$-$C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6$-$C_{10})$-aryl and —$(C_6$-$C_{10})$-aryl-$(C_6$-$C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

The expression "—$(C_3$-$C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl or adamanty.

One example of a substituted cycloalkyl would be menthyl.

The expression "—$(C_3$-$C_{12})$-heterocycloalkyl groups", in the context of the present invention, encompasses nonaromatic, saturated or partly unsaturated cycloaliphatic groups having 3 to 12, especially 5 to 12, carbon atoms. The —$(C_3$-$C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— or —S(=O)—. Examples of —$(C_3$-$C_{12})$-heterocycloalkyl groups are tetrahydrothiophenyl, tetrahydrofuryl, tetrahydropyranyl and dioxanyl.

The invention is further illustrated in detail below by examples without the invention being limited to the working examples.

General Methods
Solvents and Reagents

All reactions with moisture- and/or oxygen-sensitive substances were carried out in baked-out apparatuses under an argon atmosphere. Solvents for extraction and column chromatography were used at the following purities: dichloromethane (99.9%, Walter, Cat. No. BIE 073107033) ethyl acetate (99.5%, Walter, Cat. No. BIE 003917025) and n-hexane (95%, Walter (Baker), Cat. No. 8669),
n-heptane (95%, Walter (Baker), Cat. No. 8662). Other solvents for extraction and column chromatography were of technical quality and were used without further purification unless otherwise stated. Dry solvents (abs.) were purified using a Pure Solv MD-7 System and stored under an argon atmosphere. Benzyl bromide was freshly distilled (17 mbar/82° C.) prior to use. Deuterated solvents were distilled from the drying agents specified: dichloromethane-$d_2$ (phosphorus pentoxide), toluene-$d_8$ (1. KOH; 2. sodium). Chemicals used for the syntheses were supplied by Sigma Aldrich, Alfa Aesar, Acros Organics, Avantor Performance Materials B.V., Merck KGaA and ABCR GmbH & Co. KG. These were used without further purification unless otherwise stated.

Analysis

IR Spectroscopy:

IR spectra were recorded with a Nicolet 6700 FT-IR spectrometer from Thermo Electron. The substances were measured by ATR methods.

$^1$H NMR Spectroscopy.

$^1$H NMR spectra were recorded with a model AV 300 (300 MHz) and with the model Fourier 300 (300 MHz) from Bruker. Chemical shifts are stated in units on the δ-scale. The residual proton signals of the solvent (dichloromethane-$d_2$: δ=5.32 ppm, toluene-$d_8$: δ=7.09; 7.00; 6.98; 2.09 ppm) served as standard.

13C NMR Spectroscopy:

13C NMR spectra were recorded with models AV 300 (75 MHz) and Fourier 300 (75 MHz) from Bruker. The signal of the solvent (dichloromethane-$d_2$: δ=54.0 ppm, toluene-$d_8$: δ=137.9; 129.2; 128.3; 125.5; 20.4 ppm) served as internal standard wherein the chemical shifts were taken from the broadband 1H-decoupled spectra.

77Se NMR Spectroscopy:

77Se NMR spectra were recorded with an AV 300 (57 MHz) from Bruker. The spectra were measured in broadband 1H-decoupled mode. The chemical shifts are reported in ppm.

Mass Spectrometry:

EI mass spectra were recorded on a Finnigan MAT 95-XP instrument from Thermo Electron and ESI-TOF mass spectra with a model 6210 Time-of-Flight LC/MS from Agilent.

Autoclave Experiments of Rhodium-Catalysed Hydroformylation

The hydroformylation was conducted in a 200 ml autoclave equipped with pressure-retaining valve, gas flow meter, sparging stirrer and pressure pipette from Premex Reactor AG, Lengau, Switzerland. The toluene used as solvent was purified using a Pure Solv MD-7 System and stored under argon. The 1-octene or n-octenes substrate (EVONIK Industries AG, octene isomer mixture of 1-octene: 3.3%; cis+trans-2-octene: 48.5%; cis+trans-3-octene: 29.2%; cis+trans-octene-4: 16.4%; structurally isomeric octenes: 2.6%) used as substrate was heated at reflux over sodium for several hours and distilled under argon.

For the experiments, solutions of the catalyst precursor and the ligand were mixed in the autoclave under an argon atmosphere. [(acac)Rh(COD)] (Umicore, acac=acetylacetonate anion; COD=1,5-cyclooctadiene) was used as catalyst precursor. For experiments at a concentration of 100 ppm-m rhodium, 10 ml of a 4.31 mM solution was placed in the autoclave. Subsequently, the mass of ligand corresponding to a ratio L/Rh=5:1 (or 1:1) was dissolved and mixed in 10 ml of toluene. By adding further toluene, the starting volume of the catalyst solution was adjusted to 41.0 mi. Into a pressure-resistant pipette was filled: 1-octene or n-octenes (10.70 g). The autoclave was heated while stirring (1500 rpm) to the temperatures stated in each case at a total gas pressure (synthesis gas: Linde; $H_2$ (99.999%):CO (99.997%)=1:1) of a) 42 bar for a final pressure of 50 bar or b) 12 bar for the final pressure of 20 bar. After reaching the reaction temperature, the synthesis gas pressure was increased to a) 48.5 bar for a final pressure of 50 bar or b) 19.5 bar for a final pressure of 20 bar and the reactant was introduced under a positive pressure of about 3 bar set in the pressure pipette. The reaction was conducted at a constant pressure of 50 or 20 bar (closed-loop pressure controller from Bronkhorst, the Netherlands) respectively over 4 h. After the reaction time had elapsed, the autoclave was cooled to room temperature, decompressed while stirring and purged with argon. 1.0 ml of each reaction mixture was removed immediately after the stirrer had been switched off, diluted with 5.0 ml of pentane and analysed by gas chromatography: HP 5890 Series II plus, PONA, 50 m×0.2 mm×0.5 μm.

Some abbreviations: Bn=Benzyl; calc.=calculated; MOM=Methylmethoxy;

Synthesis of the Precursors:

General Procedure—Diphenol Selenides, Structure (IX)

8.2 mmol of the particular phenol are dissolved in the appropriate solvent (8.2 m). The reaction mixture is heated, and 4.9 mmol of selenium dioxide are added while stirring. The solvent is distilled under reduced pressure (temperature <70° C.). A frit is prepared with 2.5 cm of silica gel (at the bottom) and 2.5 cm of zeolite (at the top). The distillation residue is taken up in the eluent and applied to the filtration column. Cyclohexane:ethyl acetate (95:5) is used to wash the product off the frit and collect it in fractions. The fractions containing the product are combined and freed of the eluent by distillation. The fractions obtained are recrystallized from 95:5 cyclohexane:ethyl acetate. For this purpose, the solid residue is dissolved at 50° C., and insoluble residues are filtered off using a glass frit. The reaction product crystallizes out of the saturated solution at room temperature overnight. The resulting crystals are washed once again with cold cyclohexane.

The structural formula shows the main product obtained in each reaction.

Bis(3,5-dimethyl-2-hydroxyphenyl)selenium; Structure IX, 1a

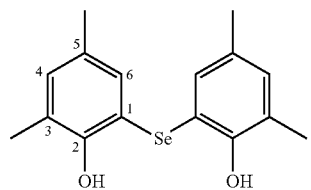

The reaction is conducted according to the general procedure in a screw-top test tube. For this purpose, 1.00 g (8.2 mmol, 1.0 equiv.) of 2,4-dimethylphenol and 0.54 g (4.9 mmol, 0.6 equiv.) of selenium dioxide are dissolved in 1 ml of pyridine and heated. The product is obtained as a colourless crystalline solid.

1H NMR (400 MHz, $CDCl_3$): δ (ppm)=7.12 (s, 2H, 6-H), 6.91 (s, 2H, 4-H), 5.97 (s, 2H, OH), 2.23 (s, 6H, 3-$CH_3$) 2.23 (s, 6H, 5-$CH_3$); 13C NMR (100 MHz, $CDCl_3$): δ (ppm)= 151.7 (C-2), 133.2 (C-3), 133.1 (C-5), 130.4 (C-4), 124.2 (C-6), 114.9 (C-1), 20.3 (5-$CH_3$), 16.5 (3-$CH_3$); 77Se NMR (76 MHz, $CDCl_3$): δ (ppm)=163.36 ppm.

Bis(3-tert-butyl-5-methyl-2-hydroxyphenyl)selenium, Structure IX, 1b

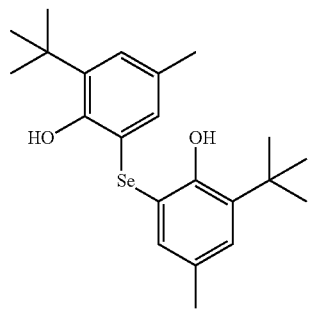 [SMILES: Cc1cc([Se]c2cc(C)cc(C(C)(C)C)c2O)c(O)c(C(C)(C)C)c1]

The reaction is conducted according to the general procedure in a screw-top test tube. For this purpose, 1.32 g (8.0 mmol, 1.0 equiv.) of 2-tert-butyl-4-methylphenol and 0.54 g (4.9 mmol, 0.6 equiv.) of selenium dioxide are dissolved in 1 ml of pyridine and heated.

1H NMR (300 MHz, $CDCl_3$): δ (ppm)=7.15 (s, 2H, 6-H), 7.05 (s, 2H, 4-H), 5.07 (s, 2H, OH), 2.21 (s, 6H, 5-$CH_3$), 2.21 (s, 18H, 3-C(CH$_3$)$_3$; $^{13}$C NMR (75 MHz, CDCl$_3$): δ (ppm)=152.1, 136.4, 133.4, 120.1, 129.5, 117.2, 35.1, 29.6, 20.8.

3,3',5,5'Tetra-tert-butylbiphenyl-2,2'-diol, Structure IX, 1c

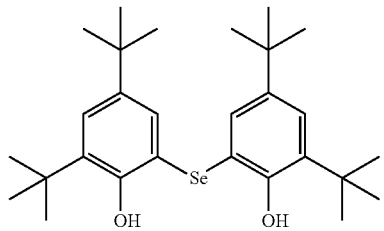 [SMILES: CC(C)(C)c1cc([Se]c2cc(C(C)(C)C)cc(C(C)(C)C)c2O)c(O)c(C(C)(C)C)c1]

The reaction is conducted according to the general procedure in a screw-top test tube. For this purpose, 1.67 g (8.2 mmol, 1.0 equiv.) of 2,4-di-tert-butylphenol and 0.55 g (4.9 mmol, 0.6 equiv.) of selenium dioxide are dissolved in 1 ml of pyridine and heated.

$^1$H NMR (400 MHz, CDCl$_3$): δ (ppm)=7.31 (d, J=2.4 Hz, 2H), 7.29 (d, J=2.4), 6.29 (s, 2H), 1.42 (s, 18H), 1.24 (s, 18H); $^{13}$C NMR (75 MHz, CDCl$_3$): δ (ppm)=151.7, 143.5, 135.8, 129.8, 125.6, 117.2, 35.4, 34.4, 31.6, 29.7.

Biphenols:

The biphenols can be synthesized analogously to DE102013203865 and DE102013203867.

Synthesis of the Chlorophosphites:

The synthesis of the monochlorophosphites such as 6-chlorodibenzo[d,f][1,3,2]dioxaphosphepine is known to a person skilled in the art and is carried out in a known manner. Chlorophosphites can be prepared from the corresponding dihydroxyl compounds by addition of phosphorus trichloride in the presence of a base. For further information see also "Phosphorus(III) Ligands in Homogeneous Catalysis—Design and Synthesis" by Paul C. J. Kamer and Piet W. N. M. van Leeuwen; John Wiley and Sons, 2012; including p. 94 ff, and references cited therein.

Synthesis of 6-chlorodibenzo[d,f][1,3,2]dioxaphosphepine IX, 2a

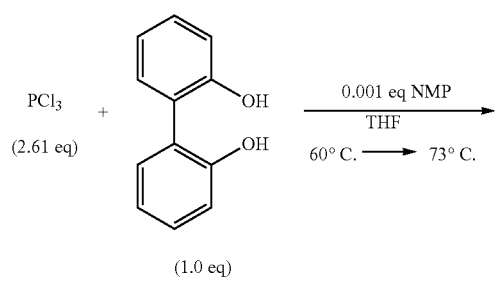

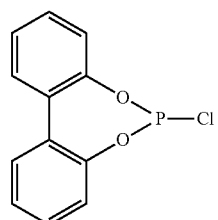

2a

A baked-out 100 ml three-neck flask having a reflux condenser, internal thermometer and dropping funnel was initially charged with 913 µl (1.43 g, 10.4 mmol, 2.61 eq.) of phosphorus trichloride at RT, and 3.80 µl of N-methyl-2-pyrrolidinone were added. The reaction mixture was heated to an internal temperature of 60° C. In a separate 10 ml Schlenk vessel, 745 mg (4.00 mmol, 1.0 eq.) of 2,2-biphenol were dissolved in 20 ml of abs. THF and added to the boiling reaction solution within 15 minutes. The latter was rinsed in with 2.0 ml of abs. THF and the mixture was heated to an internal temperature of 73° C. After a reaction time of 90 minutes, the light brown solution was cooled down to RT and the solvent was removed under reduced pressure. The brown liquid was admixed with 10 ml of abs. THF and the precipitate formed was removed by filtering. The solvent was removed again under reduced pressure and the crude product was dried under vacuum at 50° C. for three hours. 962 mg (3.85 mmol, 96%, 99% pure) of the title compound 2a were obtained as a dark brown liquid.

IR (ATR): $\hat{v}$ (cm$^{-1}$)=3064; 3027; 2924; 2848; 2435; 1919; 1601; 1565; 1498; 1474; 1432; 1295; 1273; 1244; 1194; 1172; 1116; 1094; 1042; 1010; 942; 904; 855; 760; 738; 708; 614; 597; 579; 530; 514; 486; 470; 451; 428; $^1$H NMR (300 MHz, toluene-d$_8$): δ (ppm)=7.29-6.83 (m, 8H, Ar—CH); $^{13}$C NMR (75 MHz, toluene-d$_8$): δ (ppm)=149.3 (d, J=5.7 Hz); 137.1; 130.9 (d, J=3.5 Hz); 130.0 (d, J=1.6 Hz); 129.3; 126.0 (d, J=1.2 Hz); 122.0 (d, J=2.2 Hz); $^{31}$P NMR (122 MHz, toluene-d$_8$): δ (ppm)=180.5; C$_{12}$H$_8$ClO$_2$P (250.00 g/mol).

According to the above experimental method, it is possible to prepare the following monochlorophosphites of the structure IX according to Table 1:

TABLE 1

Monochlorophosphites IX

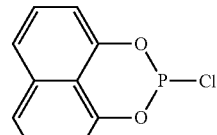

2b
(2.16 eq)

Chloronaphtho[1,8-de][1,3,2]dioxaphosphinine

TABLE 1-continued

Monochlorophosphites IX

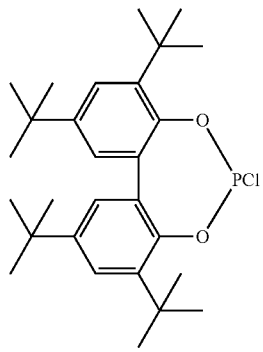

2,2′-Bis(3,5-di-tert-butyl)
phenolchlorophosphite

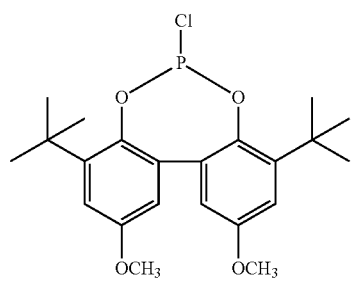

4,8-Di-tert-butyl-6-chloro-2,10-
dimethoxydibenzo[d,f][1,3,2]
dioxaphosphepine

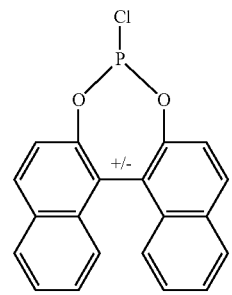

rac-4-Chlorodinaphtho[2,1-d:1′,2′-
f][1,3,2]dioxaphosphepine

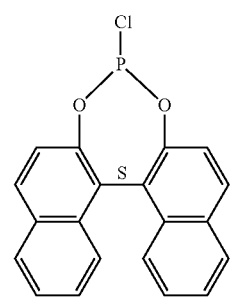

4-Chloro-S-dinaphtho[2,1-d:1′,2′-
f][1,3,2]dioxaphosphepine

TABLE 1-continued

Monochlorophosphites IX

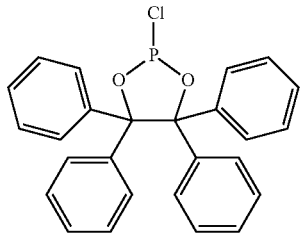

2-Chloro-4,4,5,5-tetraphenyl-
1,3,2-dioxaphospholane

The Synthesis of the Selenium Bisphosphites

Synthesis of bis(2-dibenzo[d,f][1,3,2]dioxaphosphe-pin-6-yloxy)-3,5-dimethylphenyl)selane, I (3a) and 2-((2-(dibenzo[d,f][1,3,2]dioxaphosphepin-6-yloxy)-3,5-dimethylphenyl)selanyl)-4,6-dimethylphenol, I (3b)

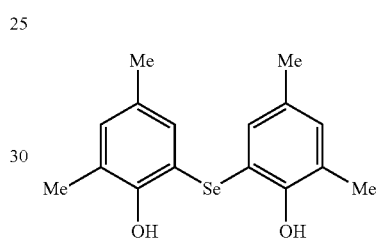

1a
(1.0 eq)

+

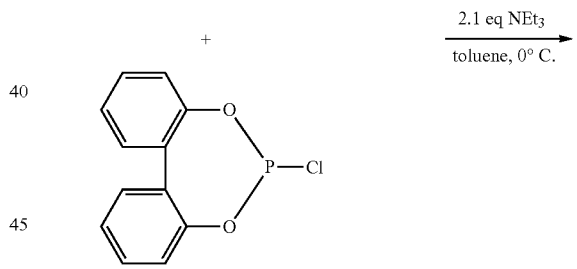

2a
(1.1 eq)

$\xrightarrow{\text{2.1 eq NEt}_3}{\text{toluene, 0° C.}}$

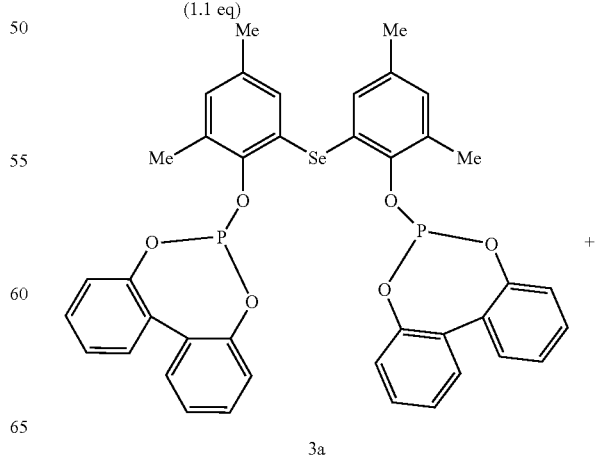

3a

+

-continued

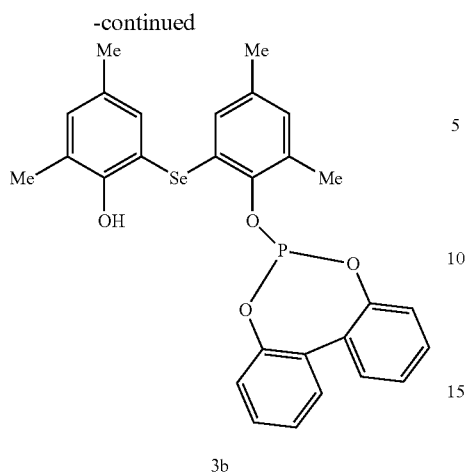

3b 500 mg (1.56 mmol, 1.0 eq) of selenodiphenol 1a and 460 µl (335 mg, 3.32 mmol, 2.13 eq) of triethylamine were dissolved in 10 ml of abs. toluene and cooled to 0° C. Subsequently, 858 mg (3.42 mmol, 2.2 eq, 90% pure) of 6-chlorodibenzo-[d,f][1,3,2]dioxaphosphepine 2a were added dropwise, forming a jelly-like precipitate. The reaction solution was stirred at room temperature overnight and filtered through silica gel, and the solvent was removed under reduced pressure. The solids obtained were dried at 50° C. under reduced pressure for three hours. 1.17 g (1.56 mmol, 100%) of a colourless solid were obtained as the crude product. 150 mg of the crude product was purified by column chromatography (2:1 H/tol.) and gave 83.3 mg of the substance mixture of the title compounds 3a (88% pure in the $^{31}$P NMR) and 3b.

HR-MS (ESI-TOF): calc. for $C_{40}H_{33}O_6P_2Se$ ([M+H]$^+$): 751.09160, found: 751.09143; calc. for $C_{40}H_{33}O_6P_2SeNa$ ([M+Na]$^+$): 773.07355, found: 773.07337.

Synthesis of bis(3,5-dimethyl-2-(naphtho[1,8-de][1,3,2]dioxaphosphinin-2-yloxy)phenyl)selane, I 3c

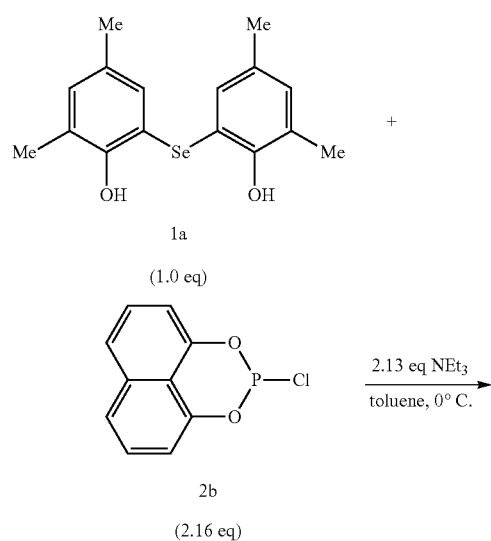

-continued

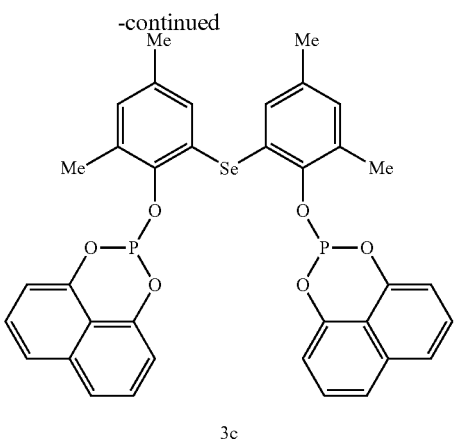

3c 532 mg (1.66 mmol, 1.0 eq) of selenodiphenol 1a and 490 µl (357 mg, 3.530 mmol, 2.13 eq) of triethylamine were dissolved in 10 ml of abs. toluene and cooled to 0° C. Subsequently, 804 mg (3.58 mmol, 2.16 eq, 92% pure) of 2-chloronaphtho-[1,8-de][1,3,2]dioxaphosphinine 2b were added dropwise, forming a jelly-like precipitate. The latter was rinsed in with 1.0 ml of abs. toluene and stirred at room temperature overnight. The reaction mixture was filtered for complete removal of the precipitate formed, the solids were washed with 20 ml of abs. toluene, and the solvent was removed under reduced pressure. The colourless oil was dried at 50° C. under reduced pressure for three hours, taken up in 45 ml of n-heptane and dried at RT overnight. The colourless precipitate formed was filtered off and dried at 50° C. under reduced pressure for three hours. 939 mg (1.35 mmol, 81%, 99% pure) of the title compound 3c were obtained as a colourless solid.

$^1$H NMR (300 MHz, dichloromethane-d$_2$): δ (ppm)=7.58 (dd, J=8.5 Hz, J=1.0 Hz, 4H. Ar—CH); 7.41 (dd, J=8.4 Hz, J=7.5 Hz, 4H, Ar—CH); 7.05-6.90 (m, 6H, Ar—CH); 6.88-6.79 (m, 2H, Ar—CH); 2.21 (d, J=0.8 Hz, 6H, —CH$_3$); 2.12 (d, J=1.2 Hz, 6H. —CH$_3$); $^{13}$C NMR (75 MHz, dichloromethane-d$_2$): δ (ppm)=148.4-147.1 (m), 144.4 (d, J=3.0 Hz); 135.5; 135.3; 132.6; 132.1; 130.9; 127.6; 124.1-122.9 (m); 122.5; 117.1 (d, J=14.1 Hz); 112.6; 20.64; 17.47; $^{31}$P NMR (122 MHz, dichloromethane-d$_2$): δ (ppm)=107.6 Hz (J$_{P,Se}$=46.8 Hz); HR-MS (ESI-TOF): calc. for $C_{38}H_{29}O_6P_2Se$ ([M+H]$^+$): 699.06023, found: 699.06008; calc. for $C_{36}H_{28}O_8P_2SeNa$ ([M+Na]$^+$): 721.04218, found: 721.04201.

Hydroformylation

Scheme 1: Presentation of the substances tested in the rhodium-catalysed hydroformylation.

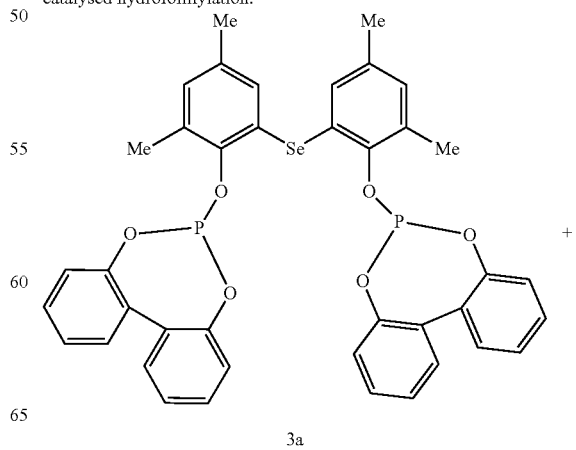

3a

-continued

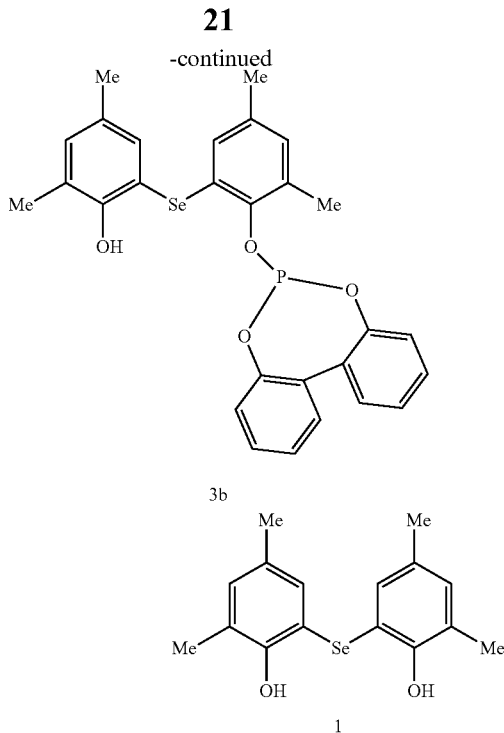

3b

TABLE 2

Presentation of the catalysis experiments using organoselenium compounds

| Entry | Ligand | Olefin/ solvent | Ratio of Rh/ ligand/olefin | p [bar] | T [° C.] | t [h] | S [%] |
|---|---|---|---|---|---|---|---|
| 1 | 3a/3b* | 1-octene/ toluene | 1:2:5461 (40 ppm Rh) | 50 | 100 | 4 | 80.3 |
| 2 | 1 | n-octene/ toluene | 1:1:2197 (100 ppm Rh) | 50 | 120 | 4 | 33.2 |

Explanations for Table 2: p = pressure, T = temperature, t = time, Y = yield; S = n-regioselectivity.
*inventive By using the selenaphosphites 3a/3b according to the invention, it is possible to achieve a yield with high n-regioselectivity of 80%.

By comparison, the rhodium-catalysed hydroformylation with selenodiphenol 1 shows a poor n-regioselectivity of 33.2%.

Through the use of the selenaphosphites 3a/3b according to the invention, the stated object was thus achieved.

The invention claimed is:

1. A compound of a heterocyclic selenaphosphite having a general structure (I)

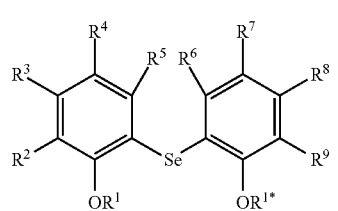

(I)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, or —N[($C_1$-$C_{12}$)-alkyl]$_2$, where the alkyl and aryl groups are each independently unsubstituted or substituted, where the respective substituted —($C_1$-$C_{12}$)-alkyl group and substituted —($C_6$-$C_{20}$)-aryl group has at least one substituent and the at least one substituent is independently selected in each case from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and where the —$R^1$ and —$R^{1*}$ groups are independently selected from —H and at least one organofunctional phosphite group, where at least one group of —$R^1$ and —$R^{1*}$ corresponds to an organofunctional phosphite group.

2. The compound according to claim 1, wherein in the heterocyclic selenaphosphite of the general structure (I)

a) at least —$R^1$ or —$R^{1*}$ corresponds to an organofunctional phosphite group and is independently selected from the structures (II), (III), (IV), (V), (VI) and (VII),

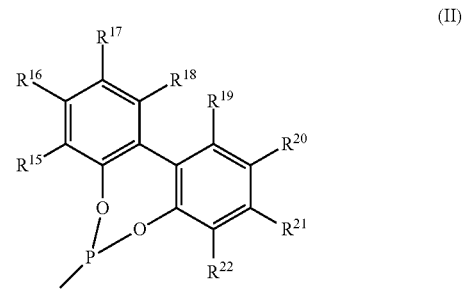

(II)

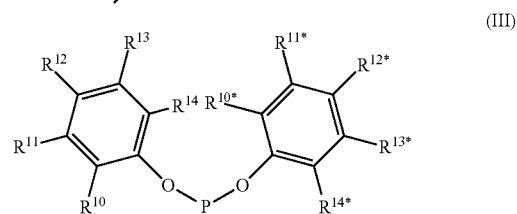

(III)

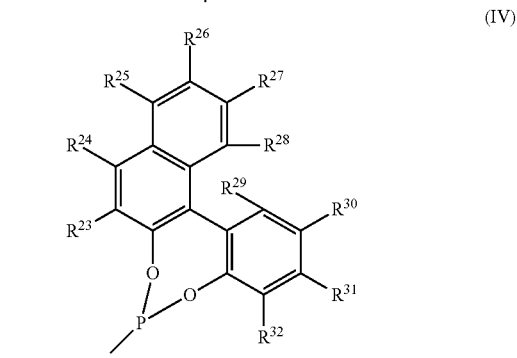

(IV)

-continued

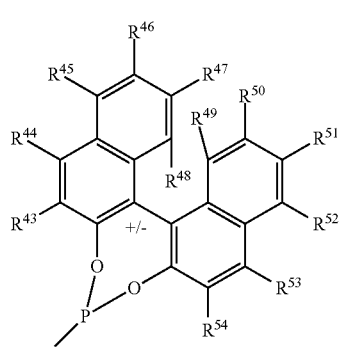
(V)

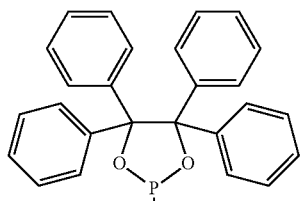
(VI)

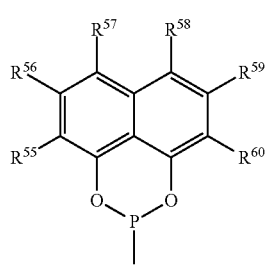
(VII)

where the radicals
$R^{15}$, $R^{16}$, $R^{17}$, $R^{18}$, $R^{19}$, $R^{20}$, $R^{21}$, $R^{22}$ in structure (II),
$R^{10}$, $R^{11}$, $R^{12}$, $R^{13}$, $R^{14}$, $R^{10*}$, $R^{11*}$, $R^{12*}$, $R^{13*}$, $R^{14*}$ in the structure (III),
$R^{23}$, $R^{24}$, $R^{25}$, $R^{26}$, $R^{27}$, $R^{28}$, $R^{29}$, $R^{30}$, $R^{31}$ and $R^{32}$ in structure (IV),
$R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure (V), and
$R^{55}$, $R^{56}$, $R^{57}$, $R^{58}$, $R^{59}$ and $R^{60}$ in structure (VII),
in the respective structure are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, or b) —$R^1$ and —$R^{1*}$ are the same and correspond to an organofunctional phosphite group and are selected from the structures (II), (III), (IV), (V), (VI) and (VII).

3. The compound according to claim 1, wherein the heterocyclic selenaphosphite of the general structure (I) is selected from the structure (Ia)

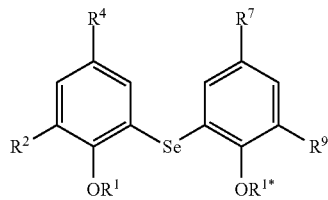
(Ia)

where $R^2$, $R^4$, $R^7$ and $R^9$ are each independently selected from:
—($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, and where —$R^1$ and —$R^{1*}$ in structure (Ia) are independently selected from —H and at least one organofunctional phosphite group, where at least —$R^1$ or —$R^{1*}$ corresponds to an organofunctional phosphite group.

4. The compound according to claim 3, wherein the —$R^1$ and —$R^{1*}$ in the heterocyclic selenaphosphite of the structure (Ia) are selected from the structures (II), (III), (IV), (V), (VI) and (VII)

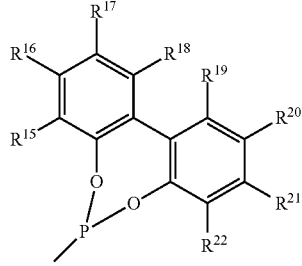
(II)

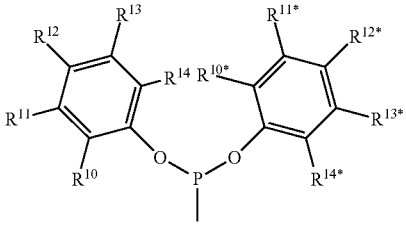
(III)

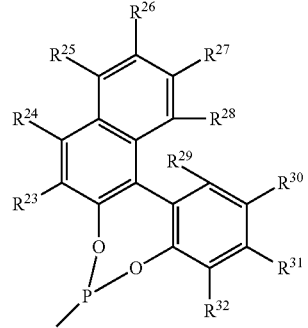
(IV)

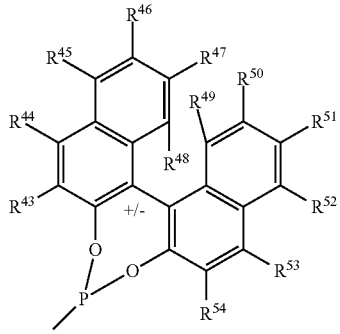
(V)

-continued

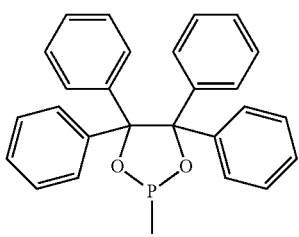
(VI)

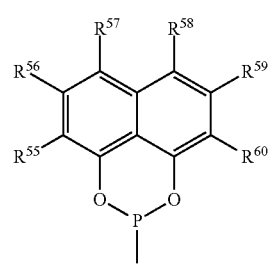
(VII)

where the radicals
$R^{15}, R^{16}, R^{17}, R^{18}, R^{19}, R^{20}, R^{21}, R^{22}$ in structure (II),
$R^{10}, R^{11}, R^{12}, R^{13}, R^{14}, R^{10*}, R^{11*}, R^{12*}, R^{13*}, R^{14*}$ in the structure (III),
$R^{23}, R^{24}, R^{25}, R^{26}, R^{27}, R^{28}, R^{29}, R^{30}, R^{31}$ and $R^{32}$ in structure (IV),
$R^{43}, R^{44}, R^{45}, R^{46}, R^{47}, R^{48}, R^{49}, R^{50}, R^{51}, R^{52}, R^{53}$ and $R^{54}$ in structure (V), and
$R^{55}, R^{56}, R^{57}, R^{58}, R^{59}$ and $R^{60}$ in structure (VII),
in the respective structure are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen.

5. The compound according to claim 1, wherein —$R^1$ and —$R^{1*}$ in the heterocyclic selenaphosphite of the structure (I) are selected from the structure (II)

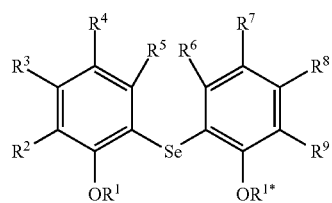
(I)

where $R^2$, $R^3$, $R^4$, $R^5$, $R^6$, $R^7$, $R^8$ and $R^9$ are each independently selected from: —H, —($C_1$-$C_{12}$)-alkyl, or —O—($C_1$-$C_{12}$)-alkyl and

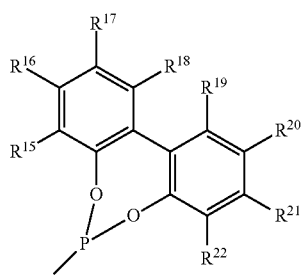
(II)

with $R^{15}, R^{16}, R^{17}, R^{18}, R^{19}, R^{20}, R^{21}, R^{22}$ in structure (II) each independently selected from: —H, —($C_1$-$C_{12}$)-alkyl, or —O—($C_1$-$C_{12}$)-alkyl, or where —$R^1$ and —$R^{1*}$ in structure (I) are independently selected from —H and at least one organofunctional phosphite group, where at least one group from —$R^1$ and —$R^{1*}$ corresponds to an organofunctional phosphite group.

6. The compound according to claim 1, wherein the —$R^1$ and —$R^{1*}$ are selected from alternative a), b), or c):
a) —$R^1$ and —$R^{1*}$ in structure (I) are the same and are selected from (II), (III), (IV), (V), (VI) and (VII):

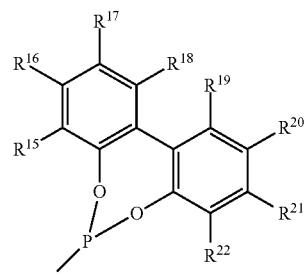
(II)

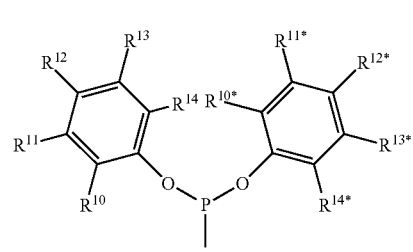
(III)

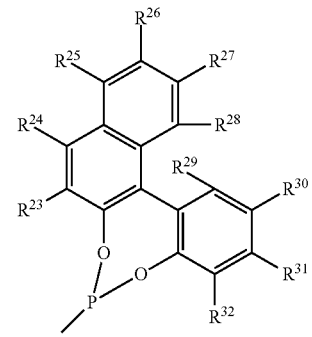
(IV)

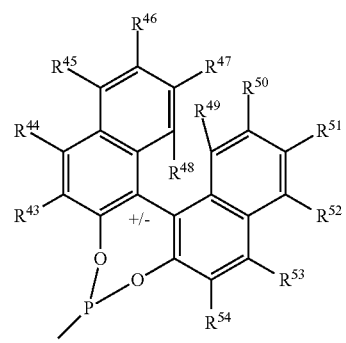
(V)

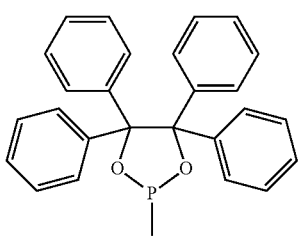
(VI)

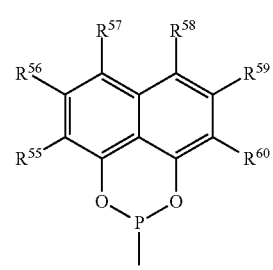
(VII)

where the radicals
$R^{15}, R^{16}, R^{17}, R^{18}, R^{19}, R^{20}, R^{21}, R^{22}$ in structure (II),
$R^{10}, R^{11}, R^{12}, R^{13}, R^{14}, R^{10*}, R^{11*}, R^{12*}, R^{13*}, R^{14*}$ in the structure (III),
$R^{23}, R^{24}, R^{25}, R^{26}, R^{27}, R^{28}, R^{29}, R^{30}, R^{31}$ and $R^{32}$ in structure (IV),
$R^{43}, R^{44}, R^{45}, R^{46}, R^{47}, R^{48}, R^{49}, R^{50}, R^{51}, R^{52}, R^{53}$ and $R^{54}$ in structure (V), and
$R^{55}, R^{56}, R^{57}, R^{58}, R^{59}$ and $R^{60}$ in structure (VII),
in the respective structure are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, b) in structure (I), —$R^1$ is —H and —$R^{1*}$ is selected from (II), (III), (IV), (V), (VI) and (VII), or c) in structure (I), —$R^{1*}$ is —H and —$R^1$ is selected from (II), (III), (IV), (V), (VI) and (VII).

7. A complex comprising
at least one compound of the general structure (I) of claim 1 or at least one compound of general structure (Ia):

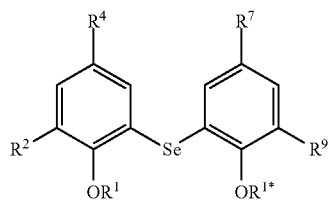
(Ia)

where $R^2$, $R^4$, $R^7$ and $R^9$ are each independently selected from:
—($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, and where —$R^1$ and —$R^{1*}$ in structure (Ia) are independently selected from —H and at least one organofunctional phosphite group, where at least —$R^1$ or —$R^{1*}$ corresponds to an organofunctional phosphite group, and
at least one metal atom selected from Rh, Ru, Co, or Ir.

8. A complex comprising: a compound according to claim 1 as a ligand and at least one metal atom.

9. A process for preparing at least one heterocyclic selenaphosphite of the general structure (I)

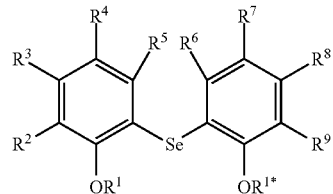
(I)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, or —N[($C_1$-$C_{12}$)-alkyl]$_2$, where the alkyl and aryl groups are each independently unsubstituted or substituted, where the respective substituted —($C_1$-$C_{12}$)-alkyl group and substituted —($C_6$-$C_{20}$)-aryl group has at least one substituent and the at least one substituent in each case is independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, and where the —$R^1$ and —$R^{1*}$ groups in structure (I) are independently selected from —H and at least one organofunctional phosphite group, where at least one group of —$R^1$ and —$R^{1*}$ corresponds to an organofunctional phosphite group, comprising at least the process step of
(i) reacting a selenodiaryl of the general structure (IX)

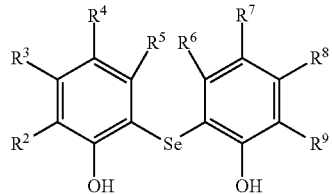
(IX)

where $R^2$, $R^3$, $R^4$, $R^5$, $R^6$, $R^7$, $R^8$ and $R^9$ are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, —S-alkyl, —S-aryl, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —$SO_3H$, —CN, or —N[($C_1$-$C_{12}$)-alkyl]$_2$, where the alkyl and aryl groups are each independently unsubstituted or substituted, where the respective substituted —($C_1$-$C_{12}$)-alkyl group and substituted —($C_6$-$C_{20}$)-aryl group has at least one substituent and the at least one substituent in each case is independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl, (ii) with at least one halophosphite compound $R^1$Hal and/or $R^{1*}$Hal, where Hal in each case is independently selected from fluorine, chlorine, bromine, or iodine, where —$R^1$ and —$R^{1*}$ each independently correspond to an organofunctional phosphite group, (iii) and obtaining at least one heterocyclic selenaphosphite of the general structure (I) or a mixture of selenaphosphites of the structure (I).

10. The process according to claim 9, wherein in the halophosphite compounds $R^1$Hal and/or $R^{1*}$Hal, where Hal in each case is independently selected from fluorine, chlorine, bromine, or iodine, and a) $—R^1$ or $—R^{1*}$ is in each case independently selected from the structures (II), (III), (IV), (V), (VI) and (VI)

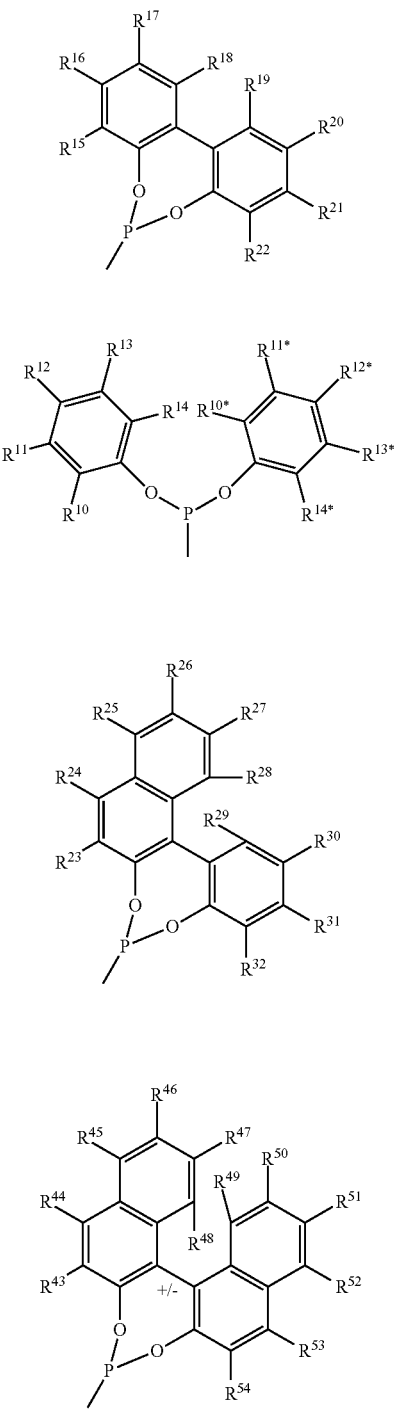

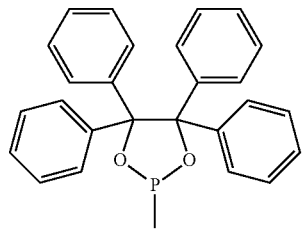

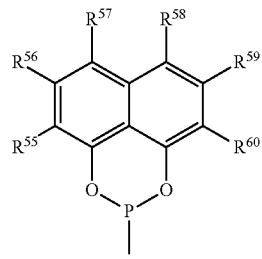

where the radicals
$R^{15}$, $R^{16}$, $R^{17}$, $R^{18}$, $R^{19}$, $R^{20}$, $R^{21}$, $R^{22}$ in structure (II),
$R^{10}$, $R^{11}$, $R^{12}$, $R^{13}$, $R^{14}$, $R^{10*}$, $R^{11*}$, $R^{12*}$, $R^{13*}$, $R^{14*}$ in the structure (III),
$R^{23}$, $R^{24}$, $R^{25}$, $R^{26}$, $R^{27}$, $R^{28}$, $R^{29}$, $R^{30}$, $R^{31}$ and $R^{32}$ in structure (IV),
$R^{43}$, $R^{44}$, $R^{45}$, $R^{46}$, $R^{47}$, $R^{48}$, $R^{49}$, $R^{50}$, $R^{51}$, $R^{52}$, $R^{53}$ and $R^{54}$ in structure (V), and
$R^{55}$, $R^{56}$, $R^{57}$, $R^{58}$, $R^{59}$ and $R^{60}$ in structure (VII),
in each case in the structures are independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen, or b) $—R^1$ and $—R^{1*}$ are the same and are selected from the structures (II), (III), (IV), (V), (VI) and (VII).

11. The process according to claim 9, wherein the halophosphite compounds $R^1$Hal and $R^{1*}$Hal are the same, and Hal is selected from chlorine and bromine, and
$—R^1$ and $—R^{1*}$ are selected from the structures (II), (III), (IV), (V), (VI) and (VII)

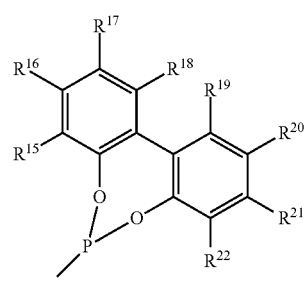

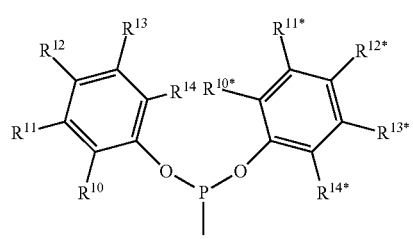

-continued

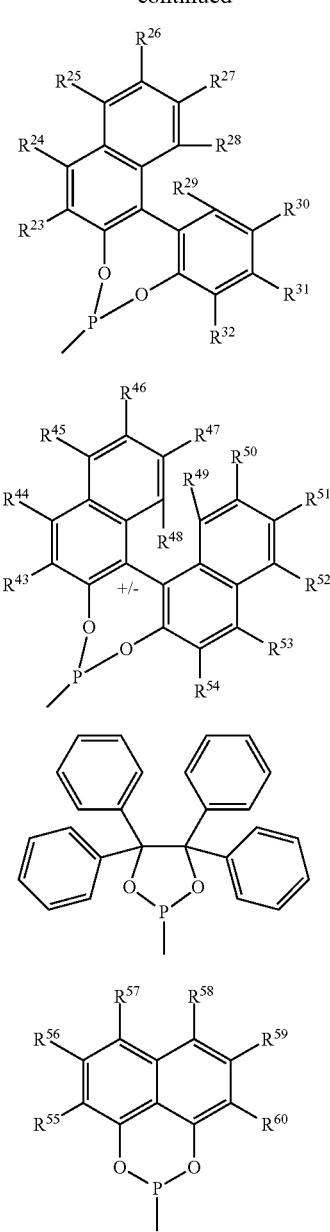

where the radicals
$R^{15}, R^{16}, R^{17}, R^{18}, R^{19}, R^{20}, R^{21}, R^{22}$ in structure (II),
$R^{10}, R^{11}, R^{12}, R^{13}, R^{14}, R^{10*}, R^{11*}, R^{12*}, R^{13*}, R^{14*}$ in the structure (III), $R^{23}, R^{24}, R^{25}, R^{26}, R^{27}, R^{28}, R^{29}, R^{30}, R^{31}$ and $R^{32}$ in structure (IV),
$R^{43}, R^{44}, R^{45}, R^{46}, R^{47}, R^{48}, R^{49}, R^{50}, R^{51}, R^{52}, R^{53}$ and $R^{54}$ in structure (V), and
$R^{55}, R^{56}, R^{57}, R^{58}, R^{59}$ and $R^{60}$ in structure (VII),
in the respective structure are each independently selected from: —H, —($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen.

12. The process according to claim 9, wherein the selenodiaryl corresponds to the general structure (IXa)

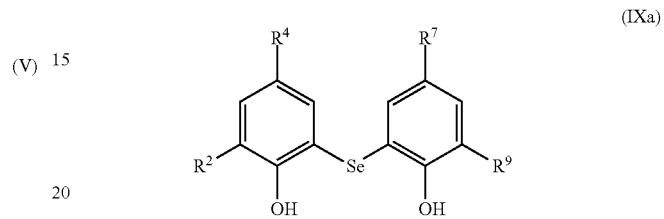

where $R^2$, $R^4$, $R^7$ and $R^9$ are each independently selected from:
—($C_1$-$C_{12}$)-alkyl, —O—($C_1$-$C_{12}$)-alkyl, —($C_6$-$C_{20}$)-aryl, —O—($C_6$-$C_{20}$)-aryl, or -halogen.

13. The process according to claim 9, wherein (i) the reaction is conducted in the presence of a base.

14. The process of claim 13, wherein (i) the reaction is conducted in the presence of an amine base or a pyridine base.

15. A process of converting an olefin to an aldehyde comprising the process steps of
(i) initially charging at least one olefin,
(ii) adding a complex according to claim 7,
and a substance including a metal atom selected from: Rh, Ru, Co, or Ir,
(iii) feeding in $H_2$ and CO to form a reaction mixture, and
(iv) heating the reaction mixture,
wherein the olefin is converted to an aldehyde.

16. A process of converting an olefin to an aldehyde comprising the process steps of
(i) initially charging at least one olefin,
(ii) adding a compound according to claim 1,
and a substance including a metal atom selected from: Rh, Ru, Co, or Ir,
(iii) feeding in $H_2$ and CO to form a reaction mixture,
(iv) heating the reaction mixture,
wherein the olefin is converted to an aldehyde.

* * * * *